United States Patent [19]
Burstein et al.

[11] Patent Number: 5,338,753
[45] Date of Patent: Aug. 16, 1994

[54] (3R,4R)-Δ6 TETRAHYDROCANNABINOL-7-OIC ACIDS USEFUL AS ANTIINFLAMMATORY AGENTS AND ANALGESICS

[75] Inventors: Sumner H. Burstein, 6 Knight Rd., Framingham, Mass. 01701; Raphael Mechoulam, Jerusalem, Israel

[73] Assignee: Sumner H. Burstein, Framingham, Mass.

[21] Appl. No.: 913,096

[22] Filed: Jul. 14, 1992

[51] Int. Cl.$^5$ ............... A61K 31/35; C07D 311/80
[52] U.S. Cl. ............................ 514/454; 549/390; 549/391
[58] Field of Search ............... 549/390, 391; 514/454

[56] References Cited

U.S. PATENT DOCUMENTS 4,973,603  11/1990  Burstein .................. 514/454

OTHER PUBLICATIONS

Burstein et al., J. Med. Chem., 35(17), 3135–41 (1992) (C.A., 117:131,3892 (1992)).

*Primary Examiner*—Nicky Chan
*Attorney, Agent, or Firm*—Pennie & Edmonds

[57] ABSTRACT

Non-psychoactive derivatives of Δ$^6$-THC-7-oic acid are described which have analgesic and anti-inflammatory properties.

18 Claims, 3 Drawing Sheets

(3R,4R)-Δ 6 TETRAHYDROCANNABINOL-7-OIC ACIDS USEFUL AS ANTIINFLAMMATORY AGENTS AND ANALGESICS

INTRODUCTION

This invention was made with Government support under Grant Numbers DA02052 and DA06481, awarded by NIDA. The Government has certain rights in this invention.

The present invention is generally directed to non-psychoactive derivatives of tetrahydrocannabinol, which exhibit anti-inflammatory, analgesic and leukocyte antiadhesion activities. The invention covers novel derivatives of (3R,4R)-Δ$^6$-tetrahydrocannabinol-7-oic acids [hereinafter referred to as (3R,4R)-Δ$^6$-THC-7-oic acid], as well as pharmaceutical compositions containing the (3R,4R)-Δ$^6$-THC-7-oic acid derivatives. The invention further covers the use of the novel derivatives and pharmaceutical compositions as therapeutic agents in the treatment of pain and tissue inflammation.

BACKGROUND OF THE INVENTION

Δ$^1$-Tetrahydrocannabinol [THC], depicted in Formula I under alternate numbering systems, is the major psychoactive constituent of marijuana.

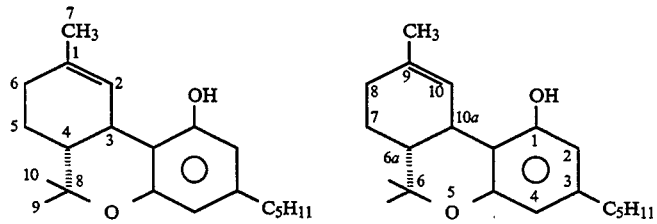

Formula I

In addition to mood-altering effects, THC has been reported to exhibit other activities, some of which may have therapeutic value. The potential therapeutic value of THC has led to a search for related compounds which, while devoid of psychoactive effects, retain the activities of potential medicinal value.

Previous work with Δ$^6$-Tetrahydrocannabinol [(3R,4R) 6a,7,10,10a-tetrahydro-6,6,9-trimethyl-3-pentyl-6H-dibenzo[b,d]pyran-1-ol, hereinafter referred to as Δ$^6$-THC], has indicated that derivatives of this compound may prove clinically useful. The 7-carboxy derivative of Δ$^6$-THC [Δ$^6$-THC-7-oic acid] has been reported to be a non-psychoactive, potent antagonist to endogenous platelet activating factor and, thus, a useful treatment for PAF-induced disorders, such as asthma, systemic anaphylaxis, and septic shock. (U.S. Pat. No. 4,973,603, issued Nov. 27, 1990 to Sumner Burstein). Another derivative, (3S,4S)-7-hydroxy-Δ$^6$-THC-1,1-dimethylheptyl, has been reported to possess analgesic and anti-emetic activities. (U.S. Pat. No. 4,876,276).

SUMMARY OF THE INVENTION

The present invention is generally directed to non-psychoactive derivatives of Δ$^6$-THC-7-oic acid, which have been shown to be potent analgesic and anti-inflammatory agents and to possess leukocyte antiadhesion activities. The invention is further related to the use of these derivatives as therapeutic agents in the treatment of pain and tissue inflammation, especially that associated with long-term illnesses such as rheumatoid arthritis.

DETAILED DESCRIPTION OF THE INVENTION

The present invention relates to (3R,4R)-Δ$^6$-Tetrahydrocannabinol-7-oic acid derivatives depicted in Formula II

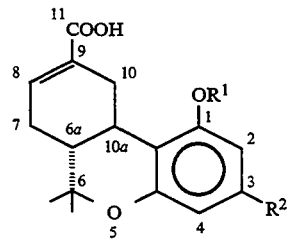

Formula II wherein R$^1$ is a hydrogen atom, —COCH$_3$ or —COCH$_2$CH$_3$; R$^2$ is a straight chain or branched C$_5$-C$_{12}$ alkyl, which may have a terminal aromatic ring; a group —(CH$_2$)$_m$-O-R$^3$, wherein m is an integer from 0 to 7 and R$^3$ is a straight chain or branched alkyl group containing from 1 to 12 carbon atoms, which may have a terminal aromatic ring; or a group CH—(CH$_3$)—(CH$_2$)$_n$—O—R$^4$, wherein n is an integer from 0 to 7 and R$^4$ is a straight chain or branched alkyl containing from 1 to 12 carbon atoms, which may have a terminal aromatic ring.

Figure 1:
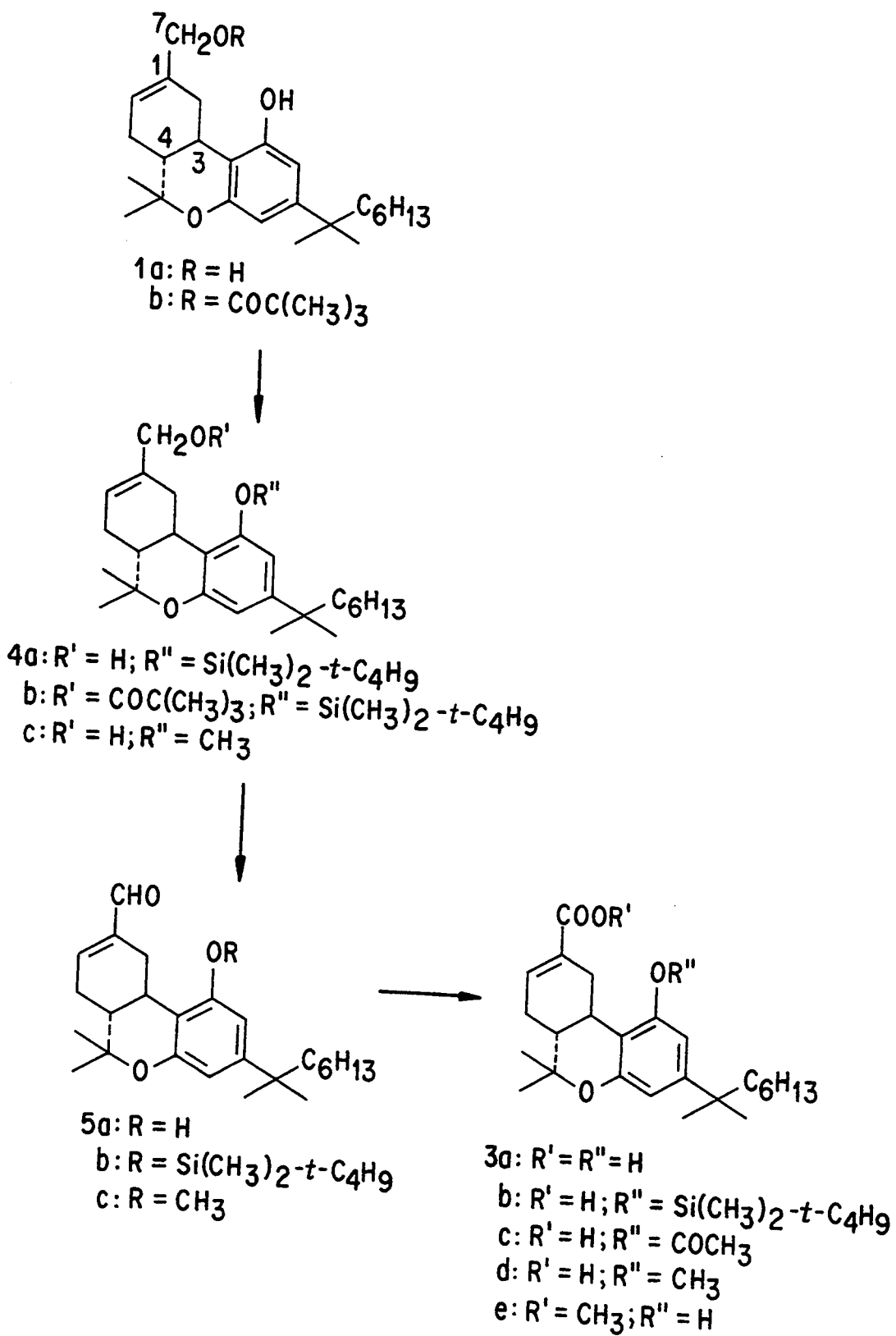
FIG. 1. Synthetic scheme for Δ$^6$-THC-7-oic acid derivatives.

Preferred compositions for uses according to the invention are obtained when R$^1$ is hydrogen and R$^2$ is 1,1-dimethylheptyl [Compound 3a in FIG. 1] and when R$^1$ is —COCH$_3$ and R$^2$ is 1,1-dimethylheptyl [Compound 3c in FIG. 1].

PREPARATION OF DERIVATIVES

The compounds of Formula II may be prepared according to the synthetic scheme depicted in FIG. 1.

In general, melting points were taken in glass capillary tubes with a Thomas-Hoover Uni-Melt apparatus. Infrared spectra were recorded on a JASCO A-200 spectrophotometer. Rotations were determined on a Perkin-Elmer Model 141 polarimeter in chloroform. Chromatographic separations were performed on silica gel columns (Woelm TSC silica, for dry chromatography, activity III/30 mm, No. 04530). The high-resolution mass spectrometry (HRMS was performed on a Varian 711 instrument.

Synthesis of Compound 4a

In general, this esterification follows the procedure of Corey and Venkateswarlu (Corey E. J. and Venkateswarlu A. "Protection of Hydroxyl Groups as Tert-Butyldimethylsilyl Derivatives." J. Am. Chem. Soc. 94:6190 (1972). Compound 1b (2.9 g, 6.17 mmol), $[\alpha]_D$ 1152.60 (c 17.2 m/mL, $CHCl_3$), prepared according to Mechoulam et al. (Mechoulam R. et al. "Synthesis of the Individual, Pharmacologically Distinct, Enantiomers of a Tetrahydrocannabinol Derivative." Tetrahydron: Asymmetry 1:315 (1990)), was dissolved in dry dimethylformamide (DMF) (6 mL). Dimethyl-tert-butylsilyl chloride (1.85g, 12.27 mmol) and imidazole (1.67 g, 24.6 mmol) were added, and the resulting mixture was stirred for 48 hours at 38 ° C. Water (30 mL) was added, and the mixture was extracted with ether. After evaporation of the dried ether layer, an oil (4b, 3.6 g) was obtained: $[\alpha]_D 153°$ (c 24.45 mg/mL, $CHCl^3$); IR $\lambda_{max}$ (neat) 1725 $cm^{-1}$, no free hydroxyl groups were observed; $^1$H NMR ($CDCl_3$) $\delta 3.28$ (1 H, br d, J=16 Hz, C-2 eq H), 4.46 (2 H, s, C-7 H), 5.70 (1 H, m, C-6 H), 6.38 (1 H, d, J=1.5 Hz, arom), 6.42 (1 H, d, J=1.5 Hz, atom). This oil (compound 4b) was used in the next step with no further purification.

A solution of compound 4b (3.2 g, 5.5 mmol) in dry ether (50 mL) was added under a nitrogen atmosphere to lithium aluminum hydride (870 mg) in dry ether (60 mL). The resulting mixture was boiled under reflux for 1.5 hours. After the standard workup (ethyl acetate followed by slow addition of a saturated solution of magnesium sulfate until a clear supernatant was formed), the ether layer was dried and evaporated to give an oil (3.2 g). The oil was chromatographed on a silica gel column (100 g), using ether-petroleum ether (6:4) as eluent, to give the alcohol 4a (8g 67%): $[\alpha]_D-175°$ (c 7.6 mg/M1, $CHCl_3$); IR $\lambda_{max}$ (neat) 3320 $cm^{-1}$ (OH band), no carbonyl bands; $^1$H NMR ($CDCl_3$) $\delta 3.38$ (1 H, br d, J=16 Hz, C-2 eq H), 4.02 (2 H, s, C-7 H), 5.72 (1 H, br d, J=16 Hz, C-2 eq H), 4.02 (2 H, s, C-7 H), 5.72 (1 H, br d, C-6 H), 6.36, 6.42 (2 H, s, atom).

Synthesis of Compound 5b

Following the procedure of Corey and Samuelsson (Corey E. J. and Samuelsson B. "One Step Conversion of Primary Alcohols in the Carbohydrate Series to the Corresponding Carboxylic-Tert-Butyl Esters." J. Org. Chem. 49:4735 (1984)), dry pyridine (2.3 mL) followed by chromic oxide (1.44 g, 14.4 mmol) was added to a solution of methylene chloride-DMF (4:1) (36 mL). The mixture was stirred for fifteen (15) minutes. The primary allylic hydroxy compound 4a (1.8g, 3.6 mmol) in methylene chloride-DMF (4:1) (7.2 mL) was added, and the reaction mixture was stirred at room temperature for one (1) hour. Ethanol (1.8 mL) was added, and the mixture was stirred for an additional ten (10) minutes and was then diluted with ethyl acetate (180 mL). The resulting mixture was filtered through a sintered-glass funnel, packed with silica (3 cm), with a layer of anhydrous sodium sulfate on top, and eluted with ethyl acetate (ca 600 mL). The ethyl acetate filtrate was washed with dilute hydrochloric acid (1 N) and then with sodium bicarbonate solution and water. After evaporation of the dried organic solvent, a semisolid compound (5b, 1.7 g, 95%) was obtained. Crystallization from pentane gave the aldehyde 5b: mp 80°–81° C.; $[\alpha]_D-268°$ (c 6.82 mg/mL, $CHCl_3$), IR $\lambda_{max}$ 1690 $cm^{-1}$ (neat); $^1$H NMR ($CDCl_3$) $\delta$ 3.82 (1 H, br d, J=15 Hz, C-2 eq H), 6.38 and 6.42 (2 H, s, atom), 6.80 (1 H, m, C-6 H), 9.50 (1 H, s, C-7 H). Anal. ($C_{31}H_{50}O_3Si$) C, H.

Synthesis of (3R, 4R)-$\delta^6$-THC-DMH-7-oic Acid (3a)

Following the procedure described by Pellegata et al. (Pellegata R et al. "An Improved Procedure for the Synthesis of Oleuropeic Acid." Synth. Commun. 15:165 (1985)), sodium chloride (488 mg) was added portionwise with vigorous stirring to a mixture of the aldehyde 5b (498 mg, 1 mmol), 2-methyl2-butene (2.24 mL), saturated aqueous potassium dihydrogen phosphate (1.34 mL), and tert-butyl alcohol (22 mL). The reaction mixture was stirred at room temperature for five (5) hours. Water (20 mL) was added, and the mixture was extracted several times with ethyl acetate, dried, and evaporated to give the crude acid which was purified on a silica gel column (10 g, elution with 10% ether-petroleum ether) to give the acid 3b (460 mg, 89%) as an oil: $[\alpha]_D-218°$ (c 13.7 mg/mL, $CHCl_3$); IR $\lambda_{max}$ 1680 $cm^{-1}$ and a broad band in the 2800–3600 $cm^{-1}$ region, $^1$H NMR $\delta 3.75$ (1 H, br d, J=18 Hz, C-2 eq H), 6.23 (1 H, d, J=1.5 Hz, arom), 6.27 (1 H, d, J=1.5 Hz, arom), 7.00 (1 H, br d, C-6 H).

Tetrabutylammonium fluoride (0.6 mmol from a 1.0M solution in THF, Aldrich,) was added by injection under a nitrogen atmosphere to a cold solution (ice bath) of the acid 3b (280 mg, 0.54 mmol) in tetrahydrofuran (THF) (3 mL). The resulting solution was stirred at 0° C. for fifteen (15) minutes. Water was added, and the mixture was extracted several times with ether. The ether layer was dried and evaporated to give the crude product. The product was further purified by silica gel column with ether-petroleum ether (1:1) as eluent. The solid thus obtained (140 mg, 56%) was crystallized from acetonitrile to give the acid 3a: mp 112°–114° C. (sintering); $[\alpha]_D-275°$ (c 3.8 mg/mL, $CHCl_3$); IR $\lambda_{max}$ (Nujol) 1680 $cm^{-1}$ and a broad band in the 3100–3600 $cm^{-1}$ region; $^1$H NMR $\delta 3.82$ (1 H, br d, J=18 Hz, C-2 eq H), 6.22 (1 H, d, J=18 Hz, C-2 eq H), 6.22 (1 H, d, J=1.5 Hz, arom), 6.38 (1 H, d, J=1.5 Hz, arom), 7.16 (1 H, m, C-6, H) ; m/z 400(M); HRMS calculated for $C_{25}H_{36}O_4$ 400.2613, found 400.2592.

Synthesis of (3R, 4R)-$\delta^6$-THC-DMH-7-oic Acid Acetate (3c).

A solution of acid 3a (100 mg, 0.25 mmol) in pyridine (2 mL) and acetic anhydride (1 mL) was stirred overnight at room temperature. Water (5 mL) was added to hydrolyze any mixed anhydride formed. The mixture was stirred for two (2) hours and then partitioned between water and ether. The ether layer was washed with dilute HCl (to remove the pyridine) and water. The organic layer was dried and evaporated. Pure product was obtained by preparative TLC (eluent ether-petroleum ether, 60:40) and crystallization from pentane. The acetate 3c, 65 mg, melts at 120°–122° C.: $[\alpha]_D$ −265° (c 9.0 mg/mL, CHCl$_3$); IR $\lambda_{max}$ (Nujol) 1760 cm$^{-1}$ and a broad band in the 3100–3600 cm$^{-1}$ region; $^1$H NMR (CDCl$_3$) δ2.30 (3 H, s, OCOCH$_3$), 3.38 (1 H, br d, J=19 Hz, C-2 eq H), 6.56 (1 H, d, J =1.5 Hz, atom), 6.68 (1 H, d, J=1.5 Hz, arom), 7.18 (1 H, m, C-6, H) ; HRMS calculated for C$_{27}$H$_{38}$O$_4$ 442.2719, found 442.2691.

EXAMPLES

PAW EDEMA TEST FOR INFLAMMATION

The induction of paw edema, in rodents, by the injection of arachidonic acid, has been used as an experimental model for inflammation. (Calhoun W. et al. "Effect of Selected Antiinflammatory Agents and Other Drugs on Zymosan, Arachidonic Acid, PAF and Carrageenan Induced Paw Edema in the Mouse." Agents Actions 21:306–309 (1987)). Administration of non-steroidal anti-inflammatory drugs (NSAIDs) prior to induction with arachidonic acid, leads to a dose-related inhibition which may be considered predictive of clinical efficacy.

The conditions were as previously reported by Calhoun et al., and by Burstein et al. (Burstein S. et al. "Antagonism to the Actions of PAF by a Nonpsychoactive Cannabinoid." J. Pharmacol. Exper. Ther. 251:531–535 (1989)), with water being substituted for mercury as the displacement medium. PAF (1.0 μg) or arachidonic acid (1.0 mg) dissolved in 50 μL of 5% ethanol in saline, was injected subcutaneously into the plantar surface of the right hind paw of ether-anesthetized CD-1 female mice (20–25 g) obtained from Charles River Laboratories. The volume of the right foot was measured to the level of the lateral malleous by water displacement before treatment, fifteen (15) minutes after PAF injection, or thirty (30) minutes after arachidonic acid injection. The change in paw volume was calculated for each mouse and the significance for each group was determined by a paired t test.

As shown in Table 1, Compound 3a of the present invention was effective in reducing arachidonate-induced paw edema. Furthermore, Compound 3a was more effective than its enantiomer, Compound 6a, in reducing such edema.

TABLE I

| Inhibition of Arachidonic Acid-Induced Paw Edema$^a$ | | |
|---|---|---|
| Dose (mg/kg)$^b$ | 3a | 6a |
| 0.005 | 26.3(28 ± 4) | — |
| 0.010 | 52.6*(18 ± 6) | — |
| 0.025 | 56.4*(17 ± 4) | — |
| 0.050 | 73.7*(10 ± 4) | 42.1(22 ± 4) |
| 0.100 | 97.4*(0.05 ± 11) | 65.8*(13 ± 3) |
| 0.250 | 100*(0.0 ± 5) | 52.6*(18 ± 6) |
| 0.500 | 100*(0.0 ± 6) | 47.4*(20 ± 4) |

$^a$Values shown are percent inhibition of paw edema when compared to vehicle treated controls. Numbers in parentheses are the increases in paw volumes ± S.E. in μl. *95% significance by ANOVA. N = 5 mice/group.
$^b$Control mice were given peanut oil (50 μl) orally. Paw volume increase = 38 ± 4 μl.

Figure 2:
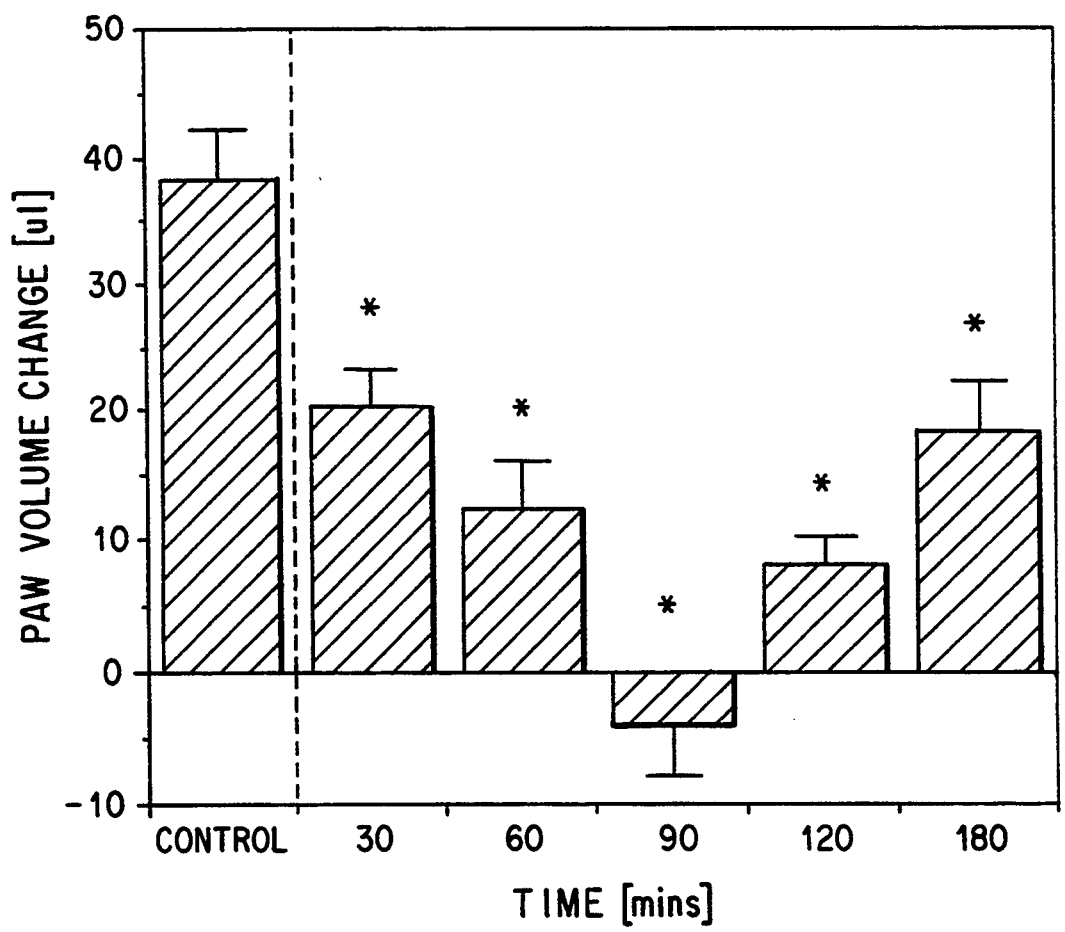
FIG. 2. Time course effect of pretreatment with Compound 3a on arachidonic acid-induced paw edema. Times shown are intervals between the oral administration of Compound 3a (0.05 mg/kg) and the injection of arachidonic acid (1.0 mg/paw). For *95% significance by ANOVA. N=5 mice per group.
Figure 3:
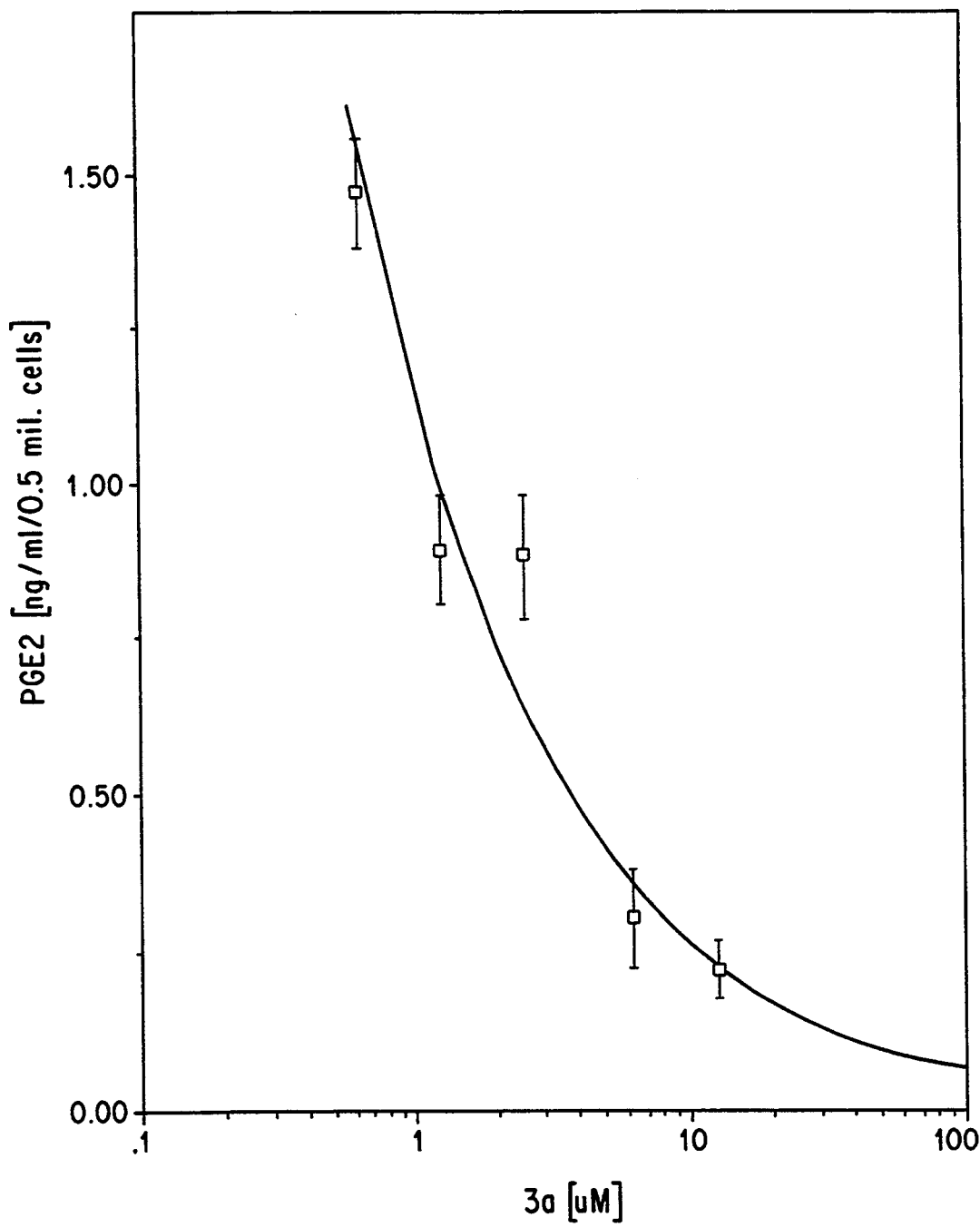
FIG. 3. Inhibition of Prostaglandin E$_2$ synthesis in mouse peritoneal cells by Compound 3a. Cells were prepared by the method of Burstein et al. J. Pharmacol. Exper. Ther. 251:531-5 (1989) and stimulated by exposure to calcium ionophore (1.0 μg/ml) for 30 minutes. The media were analyzed for PGE$_2$ by radioimmunoassay as reported by Burstein et al. Biochem. Pharmacol. 35:2553–2558 (1986). The values are the means of four replicates±S. E.

FIG. 2 shows the time course for inhibition by Compound 3a, at a dose of 0.05 mg/kg given orally. The times shown are the intervals between drug treatment and injection of 1.0 mg of arachidonic acid into the paw. A peak effect was seen at ninety (90) minutes; however, some protection remained even after three (3) hours.

As shown in Table II, Compound 3a was also effective in reducing PAF-induced edema. The greater than 100% inhibition observed with Compound 3a was unexpected and, perhaps, reflects the high anti-edema potency of the compound of the present invention. As already seen with arachidonate-induced edema, Compound 3a was also more effective than its enantiomer, 6a, in reducing PAF-induced edema.

TABLE II

| | Inhibition of PAF-Induced Paw Edema$^a$ | | | | | |
|---|---|---|---|---|---|---|
| | Dose (mg/kg)$^b$ | | | | | |
| Treatment | 0.05 | 0.10 | 0.25 | 0.5 | 1.0 | 20.0 |
| 3a | 101*(−1.2 ± 4)$^c$ | 135*(−10 ± 3)$^c$ | 150*(−14 ± 7)$^c$ | 171*(−20 ± 5)$^c$ | — | — |
| 6a | 44.4(10 ± 5)$^c$ | 38.7*(19 ± 16)$^d$ | 31.9*(21 ± 2)$^d$ | 60.1*(12 ± 7)$^d$ | — | — |
| 3e | — | 39.3*(19 ± 6)$^d$ | 63.9*(11 ± 3)$^d$ | 76.0*(7.5 ± 10)$^d$ | — | — |
| 6b | — | −44.2(38 ± 7)$^e$ | 7.6(24 ± 4)$^e$ | −7.5(28 ± 4)$^e$ | — | — |
| 1a | — | — | — | 6.3(30 ± 4)$^f$ | 56.3(14 ± 5)$^f$ | — |
| 2a | — | — | — | −37.5(44 ± 8)$^f$ | 21.8(28 ± 5)$^f$ | — |
| Δ$^6$-THC-7-oic acid | — | — | — | — | — | 50.2 |

$^a$Values shown are percent inhibition of paw edema when compared to vehicle treated controls. Numbers in parentheses are paw volume changes ± S.E. in μl. *95% significance by ANOVA. N = 8 mice/group.
$^b$Control mice were given peanut oil (50 μl) orally. Paw volume increases
$^c$28 ± 7;
$^d$31 ± 3;
$^e$26 ± 4;
$^f$32 ± 7 μl.

LEUKOCYTE ADHESION TEST

Leukocytes are thought to be major contributors to the inflammatory response, and their ability, in this regard, is reflected by their adhesion to a variety of substrates. Following the procedure of Audette and Burstein (Audette CA and Burstein S. "Inhibition of Leukocyte Adhesion by the In Vivo and In Vitro Administration of Cannabinoids." Life Sci. 47:753–759 (1983), peritoneal cells from female CD-1 mice (20–25 g) were collected at ninety (90) minutes following oral administration of Compound 3a or vehicle (50 μL of peanut oil). Cells from each treatment group (N=3) were pooled, and equal numbers of cells were aliquoted into six culture dish wells (1.9 cm$^2$ area). After incubation for 18–20 hours, nonadhering cells were removed and the remaining cell monolayer quantitated by DNA measurement. Cell viability was monitored by Trypan Blue exclusion.

As shown in Table III, Compound 3a was most effective in reducing leukocyte adhesion. This result is consistent with the results of the paw edema tests, further demonstrating Compound 3a's utility as an anti-inflammatory agent.

As shown in Table IV, Compound 3a of the present invention was an effective analgesic when measured by this test.

TABLE III

Effects on Leukocyte Adhesion[a]

| Dose (mg/kg)[b] | 1a | 2a | 3a | 6a | $\Delta^6$-THC-7-oic Acid |
|---|---|---|---|---|---|
| Control | 0.88 ± 0.08 (100) | 0.88 ± 0.08 (100) | 1.26 ± 0.05 (100) | 1.26 ± 0.05 (100) | — |
| 0.01 | — | — | 0.88 ± 0.03 (70)* | 1.34 ± 0.14 (106) | — |
| 0.05 | 1.12 ± 0.12 (127)* | 1.09 ± 0.08 (124)* | 1.34 ± 0.08 (106) | 1.29 ± 0.05 (102) | — |
| 0.10 | 0.94 ± 0.11 (106) | 0.44 ± 0.03 (50)* | 0.64 ± 0.08 (54)* | 1.38 ± 0.17 (110)* | — |
| 0.20 | 0.58 ± 0.06 (66)* | — | — | — | — |
| 0.50 | 0.59 ± 0.05 (67)* | 0.64 ± 0.06 (73)* | 0.87 ± 0.08 (69)* | 1.46 ± 0.05 (116)* | — |
| 1.00 | — | 0.59 ± 0.06 (67)* | 0.30 ± 0.03 (24)* | 0.70 ± 0.12 (56)* | — |
| Control | — | — | — | — | 0.81 ± 0.03 (100) |
| 20 | — | — | — | — | 0.67 ± 0.02 (82.7)* |
| 40 | — | — | — | — | 0.55 ± 0.02 (67.9)* |

[a]Values are the number of adhering cells × $10^6$ ± S.D. Numbers in parenthesis are percent of control. *95% significance by ANOVA; otherwise not statistically significant.
[b]Control mice were given 50 μl peanut oil orally. Peritoneal cells were collected 90 min after oral administration of the cannabinoids.

TABLE IV

Antinociceptive Effects[a]

| Dose (mg/kg) | 2a | 1a | 6b | 3e | 6a | 3a |
|---|---|---|---|---|---|---|
| .025 | — | — | — | — | 10.3(5) | 20.8(5) |
| .050 | — | — | — | — | 61.7(5)* | 85.0(5)* |
| 0.10 | — | — | — | — | 49.5(20)* | 68.3(5)*** |
| 0.25 | 30.0(5)* | 44.4(5)* | 10.4(5) | — | 61.5(17)*** | 33.4(5)* |
| 0.50 | 72.5(5)*** | 58.5(5)** | 49.0(10)* | −2.8(8) | 51.7(8)* | 34.0(5) |
| 1.0 | −10.2(5) | 106.1(5)* | 61.4(15)* | — | 14.7(5) | 28.4(5) |
| 2.0 | — | — | 37.5(10) | 42.9(9) | — | — |
| 4.0 | — | — | 3.1(10) | — | — | — |

[a]Values are the percent change in latency. Figures in brackets are the number of mice, *P<0.05; P<0.01; *P<0.005 by a paired t test; otherwise not statistically significant. Under the same conditions indomethacin (10 mg/kg) gave a 51.1% increase in latency and naproxen (40 mg/kg) produced a 64.4% increase.

HOT PLATE TEST FOR ANTINOCICEPTION

The hot-plate test is a method for measuring the analgesic activity of pharmacologic agents based on the reaction time of mice to lick their forepaws and/or jump after being placed on an aluminum hot plate heated to, and maintained at, 54°–56° C. (Kitchen I and Green PG. "Differential Effects of DFP Poisoning and Its Treatment on Opioid Antinociception in the Mouse." Life Sci. 33:669–672 (1983).

An aluminum surface was maintained at 55°±1° C. by circulating water through the passages in the metal. A clear plastic cylinder, 18 cm in diameter and 26 cm high, was placed on the surface to prevent escape. The end point was taken when the mouse either performed a hind paw lick or jumped off the surface; in no case were the animals kept more than 30 seconds on the plate. Mice were never used more than one time; control values were measured at 11 a.m. and test values at 2 p.m. Compound 3a and the other compounds were administered orally ninety (90) minutes before the hot plate test. The percent change in response time (latency) was calculated by comparing the mean of the control values with the mean of the test values and statistical significance determined by a paired t test.

MEASUREMENT OF CATALEPTIC EFFECTS

The cataleptic response was measured using the ring test described by Pertwee. (Pertwee RG. "The Ring Test. A Quantitative Method of Assessing the Cataleptic Effect of Cannabis in Mice." Br. J. Pharmacol. 46:753–763 (1972)). Mice were placed on a horizontal wire ring 5.5 cm in diameter, which was attached to a 16 cm vertical rod. The hind paws and fore paws were placed at opposite sides of the ring. It is important that the ambient temperature be maintained at 30° C. and that the environment be free of auditory stimuli and bright lights. The response was calculated as the fraction of time the mouse is immobile over a five (5) minute test period. Measurements were done between 2 p.m. and 4 p.m.

As shown in Table V, Compound 3a produced little response when compared with $\Delta^1$-THC and may be expected to be free of undesirable effects when administered long-term.

TABLE V

Cataleptic Effects in the Mouse[a]

| Treatment Response ± SD | | Dose (mg/kg) |
|---|---|---|
| Vehicle[b] | — | 7.7 ± 4.4 |

TABLE V-continued

Cataleptic Effects in the Mouse[a]

| Treatment | Dose (mg/kg) | Response ± SD |
|---|---|---|
| 1a | 0.1 | 22.9 ± 10.3* |
| 3a | 0.1 | 5.8 ± 3.4 |
| 3a | 1.0 | 12.2 ± 6.0 |
| 6a | 0.25 | 12.3 ± 10.3 |
| 6a | 0.5 | 13.8 ± 7.9 |
| 6a | 1.0 | 10.4 ± 10.6 |
| 6a | 4.0 | 8.7 ± 5.6 |
| $\Delta^6$-THC-7-oic acid | 5.0 | 10.1 ± 6.8 |
| $\Delta^6$-THC-7-oic acid | 0.5 | 10.0 ± 7.5 |
| $\Delta^1$-THC | 40 | 48.9 ± 16* |

[a]The values are expressed as the means of the fraction of time the mice remained immobile ± S.D. *95% significance by ANOVA; otherwise not statistically significant.
[b]Peanut oil (50 μl) given orally.

PHARMACOLOGICAL FORMULATIONS

The compositions of the present invention can be used in both veterinary medicine and human therapy. The compositions can be administered orally or parenterally. The form in which the drug will be administered will depend on the route by which it is administered. In one embodiment, the drug is dissolved in a vegetable oil, such as olive oil or peanut oil, and, optionally, encapsulated in a gelatin capsule. For human therapy, a preferred method of administering Formula is orally, in the form of a gelatin capsule. The dosage of the active ingredient of this invention is generally between about 10 and 500 mg per 70 kg of body weight per day, preferably between about 50 and 150 mg per 70 kg of body weight per day. The actual preferred amounts of the active ingredient will vary with each case, according to the species of mammal, the nature and severity of affliction being treated, and the method of administration. In general, the compositions of the present invention are administered to an individual, periodically, as necessary to improve symptoms of the disease being treated. The length of time during which the compositions are administered and the total dosage will necessarily vary with each case, according to the nature and severity of the affliction being treated and the physical condition of the subject.

The compositions of the present invention can be administered to an afflicted individual in the form of a pharmaceutical composition containing an effective anti-inflammatory or analgesic amount of Formula in a pharmacologically acceptable carrier, for example, a gelatin capsule, or edible oil (e.g., a vegetable oil) for oral administration, or sterile saline solution for parenteral administration. A pharmaceutical composition to be administered orally in tablet form can include, in addition to the active ingredient of the claimed invention, a filler (e.g., lactose), a binder (e.g., carboxymethylcellulose, gum arabic, gelatin), an adjuvant, a flavoring agent, a coloring agent, and a coating material (e.g., wax or plasticizer). Those skilled in the art will know, or will be able to ascertain with no more than routine experimentation, appropriate pharmacological carriers for said pharmaceutical compositions.

Those skilled in the art will recognize, or be able to ascertain using no more than routine experimentation, many equivalents to the specific embodiments of the invention described herein. Such equivalents are intended to be encompassed by the following claims.

What is claimed is:
1. A compound of the formula

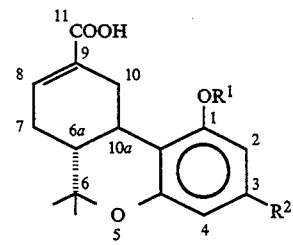

wherein $R^1$ is a hydrogen atom, —COCH$_3$ or —COCH$_2$CH$_3$; $R^2$ is a branched $C_5$-$C_{12}$ alkyl.

2. A compound according to claim 1, wherein $R^1$ is hydrogen and $R^2$ is 1,1-dimethylheptyl.

3. A compound according to claim 1, wherein $R^1$ is —COCH$_3$ and $R^2$ is 1,1,-dimethylheptyl.

4. A pharmaceutical composition comprising a compound according to claim 1.

5. A pharmaceutical composition comprising a compound according to claim 2.

6. A pharmaceutical composition comprising a compound according to claim 3.

7. A method of relieving pain in a mammal comprising administering to said mammal an effective analgesic amount of a compound according to claim 1.

8. A method of relieving pain in a mammal comprising administering to said mammal an effective analgesic amount of a pharmaceutical composition according to claim 4.

9. A method of relieving pain in a mammal comprising administering to said mammal an effective analgesic amount of a compound according to claim 2.

10. A method of relieving pain in a mammal comprising administering to said mammal an effective analgesic amount of a pharmaceutical composition according to claim 5.

11. A method of relieving pain in a mammal comprising administering to said mammal an effective analgesic amount of a compound according to claim 3.

12. A method of relieving pain in a mammal comprising administering to said mammal an effective analgesic amount of a pharmaceutical composition according to claim 6.

13. A method of relieving inflammation of bodily tissue of a mammal comprising administering to said mammal an effective anti-inflammatory amount of a compound according to claim 1.

14. A method of relieving inflammation of bodily tissue of a mammal comprising administering to said mammal an effective anti-inflammatory amount of a pharmaceutical composition according to claim 4.

15. A method of relieving inflammation of bodily tissue of a mammal comprising administering to said mammal an effective anti-inflammatory amount of a compound according to claim 2.

16. A method of relieving inflammation of bodily tissue of a mammal comprising administering to said mammal an effective anti-inflammatory amount of a pharmaceutical composition according to claim 5.

17. A method of relieving inflammation of bodily tissue of a mammal comprising administering to said mammal an effective anti-inflammatory amount of a compound according to claim 3.

18. A method of relieving inflammation of bodily tissue of a mammal comprising administering to said mammal an effective anti-inflammatory amount of a pharmaceutical composition according to claim 6.

* * * * *